United States Patent [19]

Geck et al.

[11] Patent Number: 5,466,746
[45] Date of Patent: Nov. 14, 1995

[54] EMULSIONS OF ORGANOPOLYSILOXANES CONTAINING POLAR GROUPS WITH ALKYL POLYGLYCOSIDES AS EMULSIFIERS

[75] Inventors: Michael Geck; Bernward Deubzer, both of Burghausen; Christine Baumgartner, Burgkirchen; Hans-Jürgen Lautenschlager, Haiming; Johann Sejpka, Marktl, all of Germany

[73] Assignee: Wacker-Chemie GmbH, Munich, Germany

[21] Appl. No.: 205,078

[22] Filed: Mar. 3, 1994

[30] Foreign Application Priority Data

Mar. 4, 1993 [DE] Germany ............... 43 06 796.4

[51] Int. Cl.[6] ............... C08L 83/04; B01J 13/00
[52] U.S. Cl. ............... 524/837; 524/863; 252/312; 252/314; 252/321; 252/356; 252/DIG. 1; 106/287.14
[58] Field of Search ............... 252/312, 314, 252/321, 356, DIG. 1; 524/837, 863; 106/287.14

[56] References Cited

U.S. PATENT DOCUMENTS 5,057,572  10/1991  Chrobaczek et al. ............... 524/588
5,133,897   7/1992  Balzer ............... 252/312
5,268,126  12/1993  Balzer ............... 252/312

FOREIGN PATENT DOCUMENTS

| 0337354 | 10/1989 | European Pat. Off. . |
| 0398177 | 11/1990 | European Pat. Off. . |
| 0418479 | 3/1991 | European Pat. Off. . |
| 0442098 | 8/1991 | European Pat. Off. . |
| 4131551 | 3/1993 | Germany . |
| WO/9208439 | 5/1992 | WIPO . |

*Primary Examiner*—John C. Bleutge
*Assistant Examiner*—Karen A. Dean
*Attorney, Agent, or Firm*—Martin Connaughton

[57] ABSTRACT

The aqueous emulsions based on (a) 100 parts by weight of organopolysiloxanes which contain polar groups on Si—C-bonded hydrocarbon radicals and (b) not more than 50 parts by weight of alkyl polyglycosides which are stable toward high concentrations of foreign electrolytes.

4 Claims, No Drawings

EMULSIONS OF ORGANOPOLYSILOXANES CONTAINING POLAR GROUPS WITH ALKYL POLYGLYCOSIDES AS EMULSIFIERS

FIELD OF INVENTION

The present invention relates to aqueous emulsions of organopolysiloxanes containing polar groups with alkyl polyglycosides as emulsifiers.

BACKGROUND OF INVENTION

For many uses, such as, in the treatment of all types of fiber materials, high foreign electrolyte concentrations are added to aqueous emulsions of organopolysiloxanes containing polar groups. For example, emulsions of amino- and ammonium-functional organopolysiloxanes are burdened with large amounts of inorganic salts, such as magnesium salts and sodium salts, during the highgrade finishing of cotton fabrics and cotton blended fabrics. However, the emulsion should not break as a result.

Finely aqueous emulsions, which are sufficiently stable to foreign ions for many purposes, of organopolysiloxanes containing polar aminoalkyl groups with alkyl polyglycol ethers, in particular with ethoxylates of branched alcohols, as emulsifiers are described, for example, in U.S. Pat. No. 5,057,572 and EP-A-442 098. However, the aquatic toxicity of alcohol ethoxylates is considerable. Although the biological primary and total degradation of fatty alcohol ethoxylates with linear alkyl chains is relatively rapid, that of branched-chain alcohol ethoxylates is inadequately slow.

In most uses of aqueous emulsions of organopolysiloxanes, only the organopolysiloxane constituent is used and the aqueous phase, which contains the majority of the surfactants, is passed to the waste water.

Stable aqueous emulsions of polydimethylsiloxane oils and polydiphenylsiloxane oils with alkyl polyglycosides as emulsifiers are described in EP-A-418 479. Although the alkyl polyglycosides have a very good biological degradability and a low toxicity, these emulsions are only moderately stable to foreign electrolytes, as are the emulsions with alcohol ethoxylates as emulsifiers, and because of the lack of polar groups on the siloxanes, can be employed only for certain purposes.

Washing formulations for skin and hair care which comprise alkyl polyglycosides as the main component and surfactant and organopolysiloxanes containing polar groups as the care constituent are described in WO-92/08439. The weight ratio of organopolysiloxanes to alkyl polyglycosides in this case should be not greater than 1.

SUMMARY OF INVENTION

The object of the present invention is to provide aqueous emulsions, which are stable in the presence of foreign electrolytes, of organopolysiloxanes containing polar groups with the smallest possible amounts of emulsifiers, the emulsifiers having a very good biological degradability and a low toxicity.

The objects described above are achieved by the present invention by aqueous emulsions based on
(a) 100 parts by weight of organopolysiloxanes which contain polar groups on Si—C-bonded hydrocarbon radicals and
(b) not more than 50 parts by weight of alkyl polyglycosides.

In contrast to the aqueous emulsions of polydimethylsiloxane oils and polydiphenylsiloxane oils with alkyl polyglycosides, the emulsions according to the invention have a higher stability toward foreign electrolytes, such as magnesium salts and sodium salts, than corresponding emulsions in which alkyl polyglycol ethers are used as emulsifiers.

The emulsions according to the invention comprise relatively small amounts of emulsifiers, in particular not more than 40 parts by weight of alkyl polyglycosides (b) per 100 parts by weight of organopolysiloxane (a) containing polar groups, so that the pollution of the waste water is also thereby reduced. Preferably, however, at least 5, more preferably 10, parts by weight of alkyl polyglycosides (b) are employed per 100 parts by weight of organopolysiloxanes (a), in order to ensure a good stability of the emulsions.

The emulsions according to the present invention have a discontinuous oily phase which comprises the organopolysiloxanes (a) containing polar groups and a continuous aqueous phase.

The contents of organopolysiloxane (a) and of the continuous aqueous phase can be varied within wide limits, depending on the solids content required in the emulsions and microemulsions according to the invention. The content of organopolysiloxane (a) is preferably between 5 and 60% by weight, but in particular between 10 and 40% by weight, of the total weight of the emulsion.

Examples of organopolysiloxanes (a) which contain polar groups on Si—C-bonded hydrocarbon radicals are amino, ammonium, epoxide, hydroxyl, amido, mercapto, carboxyl and/or sulfonic acid groups, and salts or esters thereof.

The organopolysiloxanes (a) preferably have the general formula

$$R_n R'_m SiO_{(4-n-m)/2} \qquad (I)$$

in which

R represents identical or different, optionally substituted hydrocarbon radicals or hydrocarbonoxy radicals having in each case 1 to 18 carbon atoms, hydrogen atoms or hydroxyl radicals, R' represents identical or different Si—C-bonded substituted hydrocarbon radicals containing polar groups, n represents an integer having the value 0, 1, 2 or 3, m represents an integer having the value 0, 1, 2 or 3 with the proviso that the sum n+m has an average value of 1.8 to 2.2, and m is chosen such that the polyorganosiloxane contains at least one radical R'.

The sum n+m preferably has an average value of 1.9 to 2.1.

Examples of hydrocarbon radicals R are alkyl radicals, such as the methyl, ethyl, n-propyl, iso-propyl, n-butyl, iso-butyl, tert-butyl, n-pentyl, iso-pentyl, neo-pentyl and tert-pentyl radicals; hexyl radicals, such as the n-hexyl radical; heptyl radicals, such as the n-heptyl radical; octyl radicals, such as the n-octyl radical and iso-octyl radicals, such as the 2,2,4-trimethylpentyl radical; nonyl radicals, such as the n-nonyl radical; decyl radicals, such as the n-decyl radical; dodecyl radicals, such as the n-dodecyl radical, octadecyl radicals, such as the n-octadecyl radical; alkenyl radicals, such as the vinyl, allyl and the 5-hexen-1-yl radicals; cycloalkyl radicals, such as cyclopentyl, cyclohexyl and cycloheptyl radicals and methylcyclohexyl radicals; aryl radicals, such as the phenyl, naphthyl and anthryl and phenanthryl radicals; alkaryl radicals, such as o-, m- and p-tolyl radicals, xylyl radicals and ethylphenyl radicals; and aralkyl radicals, such as the benzyl radical and the e- and β-phenylethyl radicals.

Examples of optionally substituted hydrocarbonoxy radicals R are substituted and unsubstituted hydrocarbon radicals R according to the above mentioned examples bonded via an oxygen atom bonded directly to a silicon atom, in particular alkoxy radicals having 1 to 18 carbon atoms and phenoxy radicals, specifically the methoxy, ethoxy, n-propoxy, iso-propoxy and phenoxy radical. Preferably, not more than 5% of the radicals R are optionally substituted hydrocarbonoxy radicals.

Examples of preferred amino-functional radicals R' are radicals of the general formula

  (II)

and ammonium salts thereof which can be prepared by reaction with mineral or carboxylic acids, in which $R^1$ represents a divalent $C_1$- to $C_{18}$-hydrocarbon radical, $R^2$ represents a hydrogen atom or an optionally fluorine-, chlorine-, or bromine-substituted $C_1$- to $C_{18}$-hydrocarbon radical, a has the values 2, 3, 4, 5 or 6 and b has the values 0, 1, 2, 3 or 4.

Examples of the divalent $C_1$- to $C_{18}$-hydrocarbon radicals $R^1$ are saturated straight- or branched-chain or cyclic alkylene radicals, such as the methylene and ethylene radicals, and propylene, butylene, pentylene, hexylene, 2-methylpropylene, cyclohexylene and octadecylene radicals, or unsaturated alkylene or arylene radicals, such as the hexenylene radical and phenylene radicals, the n-propylene radical and the 2-methylpropylene radical being particularly preferred.

Examples of the hydrocarbon radicals $R^2$ are the examples mentioned for R. Examples of halogen-substituted hydrocarbon radicals $R^2$ are haloalkyl radicals, such as the 3,3,3-trifluoro-n-propyl radical, the 2,2,2,2',2',2'-hexafluoroisopropyl radical and the heptafluoroisopropyl radical, and haloaryl radicals, such as the o-, m- and p-chlorophenyl radical.

Preferably, in formula (II) above, $R^1$ represents a divalent $C_2$- to $C_6$-hydrocarbon radical, $R^2$ represents a hydrogen atom or a methyl or cyclohexyl radical, or a divalent methylene or ethylene radical, a represents the values 2 or 3 and b represents the values 0 or 1.

Particularly preferred substances are linear polydimethylsiloxanes which optionally contain as radicals R, in addition to the methyl radicals, not more than 5% of $C_1$- to $C_3$-alkoxy or hydroxyl end groups. These polydimethylsiloxanes preferably contain as radicals R' the radicals $H_2N(CH_2)_2NH(CH_2)_3$—, $H_2N(CH_2)_2NHCH_2CH(CH_3)CH_2$—, $H_2N(CH_2)_3$—,

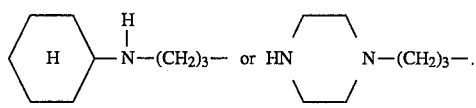

Examples of mineral acids which can be reacted with the above mentioned amino-functional hydrocarbon radicals to give the corresponding ammonium-functional radicals are hydrochloric, perchloric, sulfuric, sulfurous, nitric, nitrous, hydrofluoric, phosphoric, diphosphoric and polyphosphoric acids. Examples of suitable carboxylic acids are formic, acetic, propionic and butanoic acids, citric acid, trichloro-, dichloro- and chloroacetic acid, trifluoroacetic acid, cyanoacetic acid, phenylacetic acid, benzoic acid, m- and p-nitrobenzoic acid, oxalic acid, malonic acid and lactic acid. The ammonium-functional hydrocarbon radicals obtainable with acetic acid are particularly preferred.

Examples of amido-functional radicals are the γ-acetamidopropyl radical and partly or completely acetylated β-aminoethyl-γ-aminopropyl radicals.

Examples of epoxide-functional radicals R' are radicals of the general formulae

  (III),

  (IV), in which A represents an alkyl, alkoxyalkyl, aryl or alkaryl radical.

Examples of preferred epoxide-functional radicals R' are

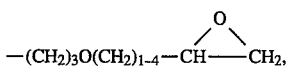

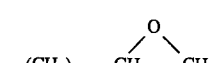

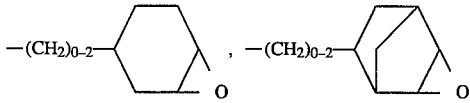

Particularly preferred epoxide-functional radicals R' are

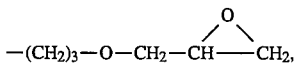

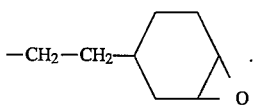

The preferred epoxide numbers of the epoxide-functional organopolysiloxanes (a) are 0.5–0.001 (equivalent/100 g), in particular 0.2–0.01 (equivalent/100 g). The epoxide number of an epoxide-functional organopolysiloxane indicates the number of equivalents of epoxide, that is to say the molar number of epoxide groups, contained in 100 grams of organopolysiloxane (a).

Examples of preferred carboxyl-functional radicals R' are radicals of the formula

  (V), and salts thereof which can be prepared by reaction with bases, in which X represents a linear, branched aliphatic, aromatic or mixed aliphatic-aromatic hydrocarbon radical, the carbon skeleton of which can be interrupted by divalent sulfur, oxygen or carboxylic acid ester radicals, and p has the value 1 or 2.

Particularly preferred carboxyl-functional radicals R' are the radicals —$(CH_2)_{4-10}$—COOH, —$CH_2CH(CH_3)$—COOH,

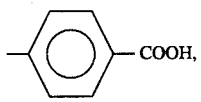

—CH$_2$CHR$^3$—S—CH$_2$—COOH, in which

R$^3$ represents a hydrogen atom or a methyl or ethyl radical, $$-(CH_2)_3O\overset{O}{\underset{\|}{C}}-(CH_2)_2-COOH,$$

$$-(CH_2)_3-\underset{\underset{CH_2-COOH}{|}}{CH}-COOH,$$

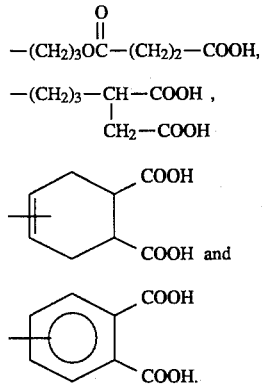

Particularly preferred carboxyl-functional radicals R' are the radicals —(CH$_2$)$_{10}$—COOH, —CH$_2$CH(CH$_3$)—COOH and —(CH$_2$)$_2$—S—CH$_2$—COOH.

Examples of bases for reaction with organopolysiloxanes (a) containing carboxyl-functional radicals R' are ammonia, amines and alkali metal and alkaline earth metal hydroxides, such as LiOH, NaOH, KOH, RbOH, CsOH, Mg(OH)$_2$, Ca(OH)$_2$, Sr(OH)$_2$, and Ba(OH)$_2$.

The preferred acid numbers of the carboxyl-functional organopolysiloxanes (a) are 1–100 (mg of KOH/g), preferably 5–50 and in particular 10–30. The acid number of a carboxyl-functional organopolysiloxane (a) indicates the number of milligrams of potassium hydroxide needed to neutralize the free acid contained in one gram of the carboxyl-functional organopolysiloxane (a).

The radicals R are preferably methyl, ethyl, phenyl, methoxy and/or vinyl radicals. Because of easier accessibility, preferably 50% of the radicals R, more preferably at least 80% of the radicals R, are methyl radicals.

One organopolysiloxane (a), preferably one of the formula (I), can be employed; it is also possible to employ a mixture of several organopolysiloxanes.

The organopolysiloxanes employed in the emulsions according to the present invention is preferably liquid. In particular, the organopolysiloxanes employed in the process according to the invention have viscosities of 100 mPa*s to 1,000,000 mPa*s, in each case measured at 25° C.

If an amino-functional organopolysiloxane is used for the preparation of the ammonium-functional organopolysiloxane (a) employed in the emulsions according to the invention, it is preferred that the amino-functional organopolysiloxane has an amine number of 0.1 to 3.0, preferably 0.2 to 0.9. The amine number of an amino-functional substance is determined as the consumption in cm$^3$ of 1N hydrochloric acid during titration of 1 g of the aminofunctional substance.

Alkyl polyglycosides which can be employed are, for example, the alkyl polyglycosides described in EP-A 418 479 of the formula $$R''-O-Z_o, \qquad (VI)$$

in which p R" represents a linear or branched, saturated or unsaturated alkyl radical having on an average of 8 to 24 carbon atoms, preferably from 8 to 16 carbon atoms, and Z$_o$ represents an oligoglycoside radical with an average of o=1 to 10, preferably 1 to 5, hexose or pentose units or mixtures thereof.

Alkyl polyglycosides with a saturated alkyl radical having an average of from 8 to 14 carbon atoms and an average degree of glycosidation n of between 1.1 and 3 are preferred.

The emulsions according to the present invention preferably have an average particle size of not more than 1 µm, in particular not more than 300 nm. The microemulsions according to the present invention preferably have an average particle size of not more than 150 nm, and more preferably not more than 20 nm. The term "emulsions" in the entire text also includes microemulsions. The term "microemulsions" relates only to emulsions having an average particle size of not more than 150 nm which are transparent to optically clear. Microemulsions of organopolysiloxanes with alkyl polyglycosides as emulsifiers have not previously been described.

To reduce the particle size and to reduce the amount of alkyl polyglycosides (b) required, the emulsions according to the present invention, in particular the microemulsions, can also comprise cosurfactants in amounts of from 0 to 30 parts by weight, in particular not more than 20 parts by weight, based on 100 parts by weight of the organopolysiloxanes (a).

Cosurfactants are understood as being polar compounds of medium molecular weight, such as C$_4$ to C$_8$ alcohols, suitable glycol ethers, amines, esters or ketones.

Examples of particularly suitable cosurfactants are 1-butanol, 2-butanol, 2-methyl-2-propanol, 1-pentanol, 2-pentanol, 3-pentanol, 1-hexanol, 2-hexanol, 3-hexanol, 1-heptanol, 2-heptanol, 3-heptanol, 4-heptanol, 1-octanol, 2-octanol, 3-octanol and 4-octanol; diethylene glycol monomethyl, -ethyl and -butylether; diethylene glycol dimethyl and -ethyl ether, 1-aminobutane, 2-aminobutane, 2-amino-2-methylpropane, 1-aminopentane, 2-amino-pentane, 1-aminohexane, 1-aminoheptane and 1-aminooctane; ethyl, propyl, isopropyl, butyl, isobutyl, pentyl, isopentyl and hexyl acetate; methyl, ethyl and tert-butyl propionate; methyl, ethyl, propyl and butyl butyrate; and 2-butanone, 2-pentanone, 3-pentanone, 4-methyl-2-pentanone, 2-hexanone, 3-hexanone, 2-heptanone, 3-heptanone, 4-heptanone, 5-methyl-3-heptanone, 2-octanone and 3-octanone.

Examples of preferred cosurfactants are 1-alkanols of the above mentioned examples having C$_5$ to C$_8$ chains, diethylene glycol monobutyl ether, diethylene glycol dimethyl and diethylene glycol diethyl ether, propyl, butyl and pentyl acetate and 2-pentanone.

Particularly preferred cosurfactants are 1-pentanol, 1-hexanol, 1-octanol, diethylene glycol monobutyl ether, diethylene glycol dimethyl ether and butyl acetate.

In addition to organopolysiloxane (a), alkyl polyglycosides (b), water and optionally, cosurfactant, the emulsions can also contain additives. Examples include bactericides, fungicides, algicides, microbicides, fragrances, corrosion inhibitors, dyestuffs, pigments, thickening agents and fillers. The emulsions according to the present invention preferably contain additives in amounts of from 0 to 1% by weight, in particular from 0 to 0.2% by weight, based on the total weight of the finished emulsion.

All the components of the emulsion according to the present invention can be mixed in any desired sequence using emulsifying apparatus or by stirring together without exerting high shearing forces. Preferably, however, a homogeneous mixture of organopolysiloxane (a), alkyl polyglycosides (b) and water is prepared first, and the mixture of cosurfactants and additives, if used, are stirred into this without exerting high shearing forces.

The pressure exerted on each of the components or mixtures is preferably the (atmospheric) pressure, increased, where appropriate, by the action of the mixing elements; the temperature which correspondingly prevails is preferably the (room) temperature, increased, where appropriate, by the action of the mixing elements.

The ammonium-functional organopolysiloxane (a) employed which is preferably contained in the emulsions according to the present invention can be prepared by addition of mineral acids or carboxylic acids to the corresponding amino-functional organopolysiloxanes. This addition of acid to the organopolysiloxane (a) can be carried out before the organopolysiloxane (a) is employed.

In a particularly preferred embodiment for the preparation of the emulsions using particularly preferred amino- and/or ammonium-functional organopolysiloxanes (a), the ammonium-functional radicals are produced in situ, during mixing of the organopolysiloxane (a), alkyl polyglycosides (b) and water by addition of the mineral and/or carboxylic acids described above, in particular acetic acid.

The emulsions according to the present invention can in principle be prepared in any turbulent mixer which has also been used to date for the preparation of emulsion. Examples of mixers which can be used are stirrers, such as paddle, straight-arm paddle, anchor, gate, screw, propeller, disk, impeller, turbine and planetary stirrers, single- and twin-screw mixers, mixing turbines, colloid mills, ultrasonic mixers, in-line mixers, pumps and homogenizers, such as high pressure, turbine and circulatory homogenizers.

The emulsions according to the invention can be employed in all instances where silicone emulsions have also hitherto been employed. They are particularly suitable as agents or as a constituent of an agent for impregnating fibres and fabrics, in cosmetics and cleaning and polishing agents, in paints or impregnating agents for building material and precursors thereof, in antifoam agents and for non-stick coatings. They can thus be used for sizing glass, ceramic and carbon fibers, for impregnating and coating textile fibers, for example as a thread lubricant, and textile fabrics, in cosmetics, such as hand creams, body lotions, shampoos, hair rinses, setting lotions and shaving creams and lotions, in polishes, such as furniture, floor and automobile polishes, in waxes, such as floor waxes, and in disinfectants, for hydrophobizing gypsum before or after shaping thereof into building components, for impregnating natural or artificial stone, concrete, cement and masonry, for hydrophobizing aerated concrete before or after foaming thereof, in paints for building work and components thereof, such as emulsion paints, in particular in silicone paints, in or as paper coatings for backings self-adhesive labels and as mold release agents for polymers.

The use of the emulsions according to the present invention, in particular the emulsions of amino-functional and ammonium-functional organopolysiloxanes (a), as agents or in agents for impregnating and coating textile fibers and fabrics is particularly preferred. The emulsions according to the invention thus impart to the textile fibers and sheet-like structures treated, a very pleasant, soft handle. In the examples which follow, unless stated otherwise, all the amounts and percentages data relate to the weight. Unless stated otherwise, the following examples are carried out under atmospheric pressure (about 0.1 mPa (absolute)) and room temperature (about 20° C.) or at temperatures and under pressures which are established when the reactants are brought together at room temperature without additional heating or cooling or by the action of mixing elements on the components or mixtures.

Amino-functional organopolysiloxanes (a):

Polysiloxane A1:

Organopolysiloxane comprising dimethylsiloxy units, methyl-(N-[2-aminoethyl]-3-aminopropyl)siloxy units and terminal methoxydimethylsilyl groups; viscosity: 1000 mPa.s at 25° C.; amine number: 0.3.

Polysiloxane A2:

Organopolysiloxane comprising dimethylsiloxy units, methyl-(N-[2-aminoethyl]-3-aminopropyl)siloxy units and terminal methoxydimethylsilyl groups; viscosity: 6500 mPa.s at 25° C.; amine number: 0.13.

Polysiloxane A3:

Organopolysiloxane comprising dimethylsiloxy units, methyl-(N-[2-aminoethyl]-3-aminopropyl)siloxy units and terminal methoxydimethylsilyl groups; viscosity: 1200 mPa.s at 25° C.; amine number: 0.6.

Carboxyl-functional organopolysiloxane A4:

Organopolysiloxane comprising dimethylsiloxy units, methyl-(2-carboxypropyl)siloxy units and terminal trimethylsilyl groups; viscosity: 2000 mPa.s at 25° C.; acid number: 17.

Epoxide-functional organopolysiloxane A5:

Organopolysiloxane comprising dimethylsiloxy units, methyl-(3-glycidyloxypropyl)siloxy units and terminal trimethylsilyl groups; viscosity: 8000 mPa.s at 25° C.; epoxide number: 0.026.

Emulsifier B:

50% strength solution in water of a $C_8$ to $C_{11}$-alkyl polyglycoside having a degree of glycosidation of 1.35, commercially obtainable under the trade name Atlas G-2541 from ICI Speciality Chemicals.

EXAMPLE 1

30 g of emulsifier B, 0.45 g of glacial acetic acid and 42.5 g of polysiloxane A1 are homogenized with an Ultra-Turra® T 45 from Janke and Kunkel. 192 g of completely desalinated water (VE water) are then incorporated into the resulting homogeneous paste using the Ultra-Turra®. A low-viscosity, finely disperse (average particle diameter 200 nm) emulsion having a silicone content of 16% is obtained, which, after standing for more than 6 months, shows no signs at all of instability and has an outstanding stability toward addition of foreign electrolytes.

EXAMPLE 2

4 g of 1-pentanol are added to 265 g of emulsion from Example 1 while simply stirring, without exerting high shearing forces. A low-viscosity, clear microemulsion (average particle diameter 7 nm) having a silicone content of 15.8% results, which, after standing for more than 6 months, shows no signs at all of instability.

Demonstration of the outstanding stability of the microemulsion from Example 2 toward addition of foreign electrolytes:

(a) Solid sodium chloride is added in 200 mg portions to 20 g of microemulsion from Example 2 at intervals of 5 minutes, while stirring and shaking. Only after a total of 3.6 g of sodium chloride has been added in the course of 90 minutes does the emulsion, which was completely clear until then, start to become cloudy.

(b) 2 g of microemulsion from Example 2 are diluted with 18 g of VE water and solid sodium chloride is added to the resulting clear microemulsion in portions as in (a). After a total of 7.0 g of sodium chloride has been added in the course of 175 minutes, the solubility limit for sodium chloride is exceeded; the microemulsion continues to be clear.

COMPARISON EXAMPLE 1

The procedure is analogous to Example 1, with the modification that instead of 30 g of emulsifier B, 15 g of an isotridecyl alcohol polyglycol ether with 6 ethyleneoxy units (100% strength), commercially obtainable as Genapol® X060 from Hoechst AG, are used. 4 g of 1-pentanol are added to 265 g of the resulting emulsion as in Example 2, while stirring, and the stability of the resulting clear microemulsion toward addition of foreign electrolytes is investigated as in Example 2.

(a) Solid sodium chloride is added in 200 mg portions to 20 g of microemulsion from Comparison Example 1 at intervals of 5 minutes, while stirring and shaking. After a total of only 0.4 g of sodium chloride has been added in the course of 10 minutes, the originally clear microemulsion shows an intensive white coloration and separates into two phases in the course of 16 hours.

(b) 2 g of microemulsion from Comparison Example 1 are diluted with 18 g of VE water and solid sodium chloride is added to the resulting clear microemulsion as in (a). After a total of only 0.8 g of sodium chloride has been added in the course of 20 minutes, clouding occurs.

EXAMPLE 3

30 g of emulsifier B, 0.38 g of glacial acetic acid and 82.5 g of polysiloxane A2 are homogenized with an Ultra-Turra® T 45 from Janke and Kunkel. 139.5 g of VE water are then incorporated into the resulting homogeneous paste with the Ultra-Turra®. A low-viscosity, finely disperse (average particle diameter 250 nm) emulsion having a silicone content of 32.7% is obtained, which, after standing for more than 6 months, shows no signs at all of instability and has a good stability toward addition of foreign electrolytes.

EXAMPLE 4

30 g of emulsifier B, 0.98 g of glacial acetic acid and 42.5 g of polysiloxane A3 are homogenized with an Ultra-Turrax® T 45 from Janke and Kunkel. 191.5 g of VE water are then incorporated into the resulting homogeneous paste with the Ultra-Turra®. A low-viscosity, transparent microemulsion (average particle diameter 51 nm) having a silicone content of 16% is obtained, which, after standing for more than 6 months, shows no signs at all of instability and has a good stability toward addition of foreign electrolytes.

EXAMPLE 5

2.3 g of diethylene glycol monobutyl ether are added to 100 g of emulsion from Example 4, while simply stirring without exerting high shearing forces. A low-viscosity, clear microemulsion (average particle diameter 15 nm) having a silicone content of 15.6% results, which, after standing for more than 6 months, shows no signs at all of instability and has a very good stability toward addition of foreign electrolytes.

EXAMPLE 6

30 g of emulsifier B, 192 g of VE water, 42.5 g of polysiloxane A1 and 0.45 g of glacial acetic acid are mixed for 1 hour using a spider, without exerting high shearing forces, and 8 g of 1-pentanol are then added, while stirring without exerting high shearing forces. A low-viscosity, clear microemulsion (average particle diameter 15 nm) having a silicone content of 15.5% results, which, after standing for more than 6 months, shows no signs at all of instability and has a good stability toward addition of foreign electrolytes.

EXAMPLE 7

30 g of emulsifier B, 42.5 g of polysiloxane A4 and 15.7 g of aqueous potassium hydroxide solution (0.7 molar) are homogenized with an Ultra-Turrax® T 50 from Janke and Kunkel. 160 g of VE water are then incorporated into the resulting homogeneous paste with the Ultra-Turra®. A low-viscosity, stable, transparent microemulsion (average particle diameter 28 nm) having a silicone content of 17.1% is obtained.

Demonstration of the very good stability of the microemulsion from Example 7 toward addition of foreign electrolytes:

2 g of microemulsion from Example 7 are diluted with 18 g of VE water, and a total of 8 g of solid sodium chloride is added to the resulting almost clear microemulsion, while stirring and shaking, the solubility limit for sodium chloride being exceeded; the microemulsion is still almost clear even after 24 hours.

COMPARISON EXAMPLE 2

The procedure is analogous to Example 7, with the modification that, instead of 30 g of emulsifier B, 19 g of an isotridecyl alcohol polyglycol ether with 10 ethyleneoxy units (80% strength in water), commercially obtainable as Arlypon® IT 10/80 from Chemische Fabrik Grünau GmbH, mixed with 11 g of VE water are employed. A low-viscosity, stable, slightly cloudy microemulsion (average particle diameter 68 nm) having a silicone content of 17.1% is obtained, and its stability toward addition of foreign electrolytes is investigated as in Example 7.

2 g of the microemulsion from Comparison Example 2 are diluted with 18 g of VE water, and a total of 8 g of solid sodium chloride is added to the resulting slightly cloudy microemulsion as in Example 7, while stirring and shaking, the solubility limit for sodium chloride being exceeded; no spontaneous increase in clouding can be detected. After 24 hours, however, separation of an oil and a significant increase in the clouding of the aqueous phase are observed.

EXAMPLE 8

30 g of emulsifier B and 42.5 g of polysiloxane A5 are homogenized with an Ultra-Turra® T 50 from Janke and Kunkel. 175 g of VE water are then incorporated into the resulting homogeneous paste with the Ultra-Turra®. A low-viscosity, stable emulsion having a silicone content of 17.2% and an average particle diameter of 370 nm is obtained.

COMPARISON EXAMPLE 3

An emulsion, which is not according to the invention, of a polydimethylsiloxane oil with an alkyl polyglycoside 3(a) is compared with an emulsion of the same oil using an alcohol ethoxylate 3(b) and the stability of the emulsions from 3(a) and 3(b) towards addition of foreign electrolytes is compared. Comparison Example 3(a) is based on Example 1 from EP-A 418 479.

(a) 23 g of emulsifier B and 50 g of a polydimethylsiloxane oil having terminal trimethylsilyl groups and a viscosity of 500 mPa.s are homogenized with an Ultra-Turra® T 50 from Janke and Kunkel; 427 g of VE water are then incorporated into the resulting homogeneous paste with the Ultra-Turrax®. A low-viscosity, finely disperse (average particle diameter 280 nm), stable emulsion having a silicone content of 10.0% is obtained.

(b) The procedure is analogous to Comparison Example 3(a), with the modification that instead of 23 g of emulsifier B, 14.5 g of an 80% strength solution in water of an isotridecyl alcohol polyglycol ether having 10 ethyleneoxy units, commercially obtainable as Arlypon® IT 10/80 from Chemische Fabrik Grünau GmbH, mixed with 8.5 g of VE water are employed. A low-viscosity, finely disperse (average particle diameter 240 nm), stable emulsion having a silicone content of 10.0% is obtained.

Investigation of the stability of the emulsions from Comparison Examples 3(a) and 3(b) toward addition of foreign electrolytes:

In each case a total of 7 g of sodium chloride is added in portions to 20 g of emulsion from Comparison Examples 3(a) and 3(b) and to 20 g of a 1:10 dilution of these emulsions, while shaking, until the solubility limit of sodium chloride is reached. In no case is a spontaneous change in the emulsions, which are already white before the start of the addition of electrolyte, to be observed during the sodium chloride addition. 5 hours after the addition of salt has ended, separations of oil are observed in all cases. The emulsions from Comparison Examples 3(a) and 3(b) show no differences in respect of their stability toward addition of electrolytes.

What is claimed is:

1. An aqueous emulsion comprising
   (a) 100 parts by weight of an organopolysiloxane which contains polar groups on Si—C-bonded hydrocarbon radicals and
   (b) at least 5 parts by weight but not more than 50 parts by weight of an alkyl polyglycoside.

2. An emulsion as claimed in claim 1, wherein the organopolysiloxane (a) has the general formula $$R_n R'_m SiO_{(4-n-m)/2} \qquad (I)$$

in which

R represents identical or different, optionally substituted hydrocarbon radicals or hydrocarbonoxy radicals having 1 to 18 carbon atoms, hydrogen atoms or hydroxyl radicals, R' represents identical or different Si—C-bonded substituted hydrocarbon radicals containing polar groups, n represents an integer having the value 0, 1, 2 or 3, m represents an integer having the value 0, 1, 2 or 3 with the proviso that the sum n+m has an average value of 1.8 to 2.2, and m is chosen such that the polyorganosiloxane contains at least one radical R'.

3. An emulsion as claimed in claim 1, wherein the polar groups bonded to Si—C-bonded hydrocarbon radicals are amino, ammonium, epoxide, hydroxyl, amido, mercapto, carboxyl and/or sulfonic acid groups and esters or salts thereof.

4. An emulsion as claimed in claim 1, which additionally comprises a cosurfactant.

* * * * *